United States Patent
Martin et al.

(10) Patent No.: US 11,912,968 B2
(45) Date of Patent: Feb. 27, 2024

(54) MICROCAVITY DISHES WITH SIDEWALL INCLUDING LIQUID MEDIUM DELIVERY SURFACE

(71) Applicant: CORNING INCORPORATED, Corning, NY (US)

(72) Inventors: Gregory Roger Martin, Acton, ME (US); Allison Jean Tanner, Portsmouth, NH (US)

(73) Assignee: CORNING INCORPORATED, Corning, NY (US)

( * ) Notice: Subject to any disclaimer, the term of this patent is extended or adjusted under 35 U.S.C. 154(b) by 249 days.

(21) Appl. No.: 16/629,665

(22) PCT Filed: Jul. 13, 2018

(86) PCT No.: PCT/US2018/041985
§ 371 (c)(1),
(2) Date: Jan. 9, 2020

(87) PCT Pub. No.: WO2020/013847
PCT Pub. Date: Jan. 16, 2020

(65) Prior Publication Data
US 2021/0062126 A1   Mar. 4, 2021

(51) Int. Cl.
*C12M 1/22* (2006.01)
*C12M 1/00* (2006.01)
*B29C 33/42* (2006.01)

(52) U.S. Cl.
CPC ............ *C12M 23/10* (2013.01); *C12M 29/00* (2013.01); *B29C 33/42* (2013.01)

(58) Field of Classification Search
CPC ........ C12M 23/10; C12M 29/00; B29C 33/42
See application file for complete search history.

(56) References Cited

U.S. PATENT DOCUMENTS

| 2,947,116 A | 8/1960 | Earle et al. |
| 3,630,849 A | 12/1971 | Land et al. |

(Continued)

FOREIGN PATENT DOCUMENTS

| AU | 2004256209 A1 | 1/2005 |
| CA | 2558946 A1 | 1/2005 |

(Continued)

OTHER PUBLICATIONS

Achilli et al, "Advances in the Formation, Use and Understanding of Multi-Cellular Spheroids", Expert Opin. Biol. Ther. (2012) 12(10):1347-1360.

(Continued)

*Primary Examiner* — William H. Beisner
*Assistant Examiner* — Danielle B Henkel
(74) *Attorney, Agent, or Firm* — Chandra J. Duncan

(57) ABSTRACT

A microcavity dish (10) for cultivating cells includes a dish body including a sidewall (16) that encloses a cell culture chamber within the dish body. The dish body has a top and a bottom (12). The bottom includes a cell culturing substrate comprising an array of microcavities (46). The sidewall includes a transition portion (30) that divides the sidewall into an upper portion and a lower portion that is offset inward relative to the upper portion defining a liquid medium delivery surface (26) that extends at least partially along an interior surface (28) of the sidewall and slopes toward the bottom.

12 Claims, 4 Drawing Sheets

(56) References Cited

U.S. PATENT DOCUMENTS

| | | | |
|---|---|---|---|
| 4,242,459 A * | 12/1980 | Chick | C12M 23/06 210/321.74 |
| 4,382,685 A | 5/1983 | Pearson | |
| 4,498,785 A | 2/1985 | De Bruyne | |
| 4,534,656 A | 8/1985 | De Bruyne | |
| 4,670,396 A | 6/1987 | Bear et al. | |
| 4,760,028 A | 7/1988 | De Bruyne et al. | |
| 4,927,764 A | 5/1990 | Lyman et al. | |
| 4,980,293 A | 12/1990 | Jeffs | |
| 5,047,347 A | 9/1991 | Cline | |
| 5,151,366 A | 9/1992 | Serkes et al. | |
| 5,171,994 A | 12/1992 | Bahraman | |
| 5,171,995 A | 12/1992 | Gast et al. | |
| 5,240,854 A | 8/1993 | Berry et al. | |
| 5,272,084 A | 12/1993 | O'Connell et al. | |
| 5,319,436 A | 6/1994 | Manns et al. | |
| 5,374,557 A | 12/1994 | Verma | |
| 5,398,837 A | 3/1995 | Degrassi | |
| 5,487,872 A | 1/1996 | Hafeman et al. | |
| 5,554,536 A | 9/1996 | Rising | |
| 5,598,262 A | 1/1997 | Jutard et al. | |
| 5,665,562 A | 9/1997 | Cook | |
| 5,693,537 A | 12/1997 | Wilson et al. | |
| 5,707,869 A | 1/1998 | Wolf et al. | |
| 5,710,043 A | 1/1998 | Pay | |
| 5,736,397 A | 4/1998 | Garcia et al. | |
| 5,759,494 A | 6/1998 | Szlosek | |
| 5,766,949 A | 6/1998 | Liau et al. | |
| 5,772,905 A | 6/1998 | Chou | |
| 5,783,440 A | 7/1998 | Stevens | |
| 5,792,653 A | 8/1998 | Weibezahn et al. | |
| 5,858,309 A | 1/1999 | Mathus et al. | |
| 5,972,694 A | 10/1999 | Mathus | |
| 6,030,829 A | 2/2000 | Dannoux et al. | |
| 6,039,972 A | 3/2000 | Barlow et al. | |
| 6,306,646 B1 | 10/2001 | Saad et al. | |
| 6,348,999 B1 | 2/2002 | Summersgill et al. | |
| 6,514,464 B1 | 2/2003 | Knebel | |
| 6,521,451 B2 | 2/2003 | Potter | |
| 6,567,675 B1 | 5/2003 | Rosen et al. | |
| 6,767,607 B2 | 7/2004 | Tanner et al. | |
| 6,811,752 B2 | 11/2004 | Barbera-Guillem | |
| 6,908,767 B2 | 6/2005 | Bader | |
| 7,470,424 B2 | 12/2008 | Kataoka et al. | |
| 7,547,547 B2 | 6/2009 | Dang et al. | |
| 7,674,346 B2 | 3/2010 | Clements et al. | |
| 7,687,262 B2 | 3/2010 | Cattadoris | |
| 7,691,369 B2 | 4/2010 | Kataoka et al. | |
| 7,727,759 B2 | 6/2010 | Ozawa et al. | |
| 7,745,209 B2 | 6/2010 | Martin et al. | |
| 7,745,210 B2 | 6/2010 | Martin | |
| 7,800,749 B2 | 9/2010 | Leblanc et al. | |
| 7,897,379 B2 | 3/2011 | Kenney et al. | |
| 7,919,319 B2 | 4/2011 | Jervis et al. | |
| 8,053,230 B2 | 11/2011 | Whittlinger | |
| 8,143,053 B2 | 3/2012 | Yerbic | |
| 8,148,152 B2 | 4/2012 | Kolossov et al. | |
| 8,158,426 B2 | 4/2012 | Wilson et al. | |
| 8,158,427 B2 | 4/2012 | Wilson et al. | |
| 8,163,537 B2 | 4/2012 | Martin et al. | |
| 8,168,432 B2 | 5/2012 | Wilson et al. | |
| 8,178,345 B2 | 5/2012 | Bennett et al. | |
| 8,273,572 B2 | 9/2012 | Martin et al. | |
| 8,318,479 B2 | 11/2012 | Domansky et al. | |
| 8,415,144 B2 | 4/2013 | Wilson et al. | |
| 8,470,589 B2 | 6/2013 | Martin et al. | |
| D685,497 S | 7/2013 | Kenney et al. | |
| 8,486,692 B2 | 7/2013 | Simon | |
| 8,597,597 B2 | 12/2013 | Deutsch et al. | |
| 8,617,879 B2 | 12/2013 | Yu et al. | |
| 8,697,443 B2 | 4/2014 | Wilson et al. | |
| 8,759,017 B2 | 6/2014 | Owen et al. | |
| 8,778,669 B2 | 7/2014 | Lacey et al. | |
| 8,846,399 B2 | 9/2014 | Martin et al. | |
| 8,906,685 B2 | 12/2014 | Takayama et al. | |
| 8,932,544 B2 | 1/2015 | Mueller et al. | |
| 9,039,883 B2 | 5/2015 | Guerrieri et al. | |
| 9,040,293 B2 | 5/2015 | Gulzow et al. | |
| 9,045,721 B2 | 6/2015 | Martin et al. | |
| 9,068,281 B2 | 6/2015 | Wu et al. | |
| 9,126,199 B2 | 9/2015 | Moritz et al. | |
| 9,169,460 B2 | 10/2015 | Cecchi | |
| D748,812 S | 2/2016 | Kenney et al. | |
| 9,260,684 B1 | 2/2016 | Egeler et al. | |
| 9,260,695 B2 | 2/2016 | Crowley et al. | |
| 9,389,187 B2 | 7/2016 | Furnas | |
| 9,436,990 B2 | 9/2016 | Otani et al. | |
| 9,493,733 B2 | 11/2016 | Giles | |
| 9,494,577 B2 | 11/2016 | McGarr et al. | |
| 9,573,128 B1 | 2/2017 | McClelland | |
| 9,587,213 B2 | 3/2017 | Morgan et al. | |
| 9,636,680 B2 | 5/2017 | Fattinger et al. | |
| 9,732,317 B2 | 8/2017 | Wilson | |
| 9,745,546 B2 * | 8/2017 | Aviles | C12M 25/14 |
| 9,790,465 B2 | 10/2017 | Bennett et al. | |
| 9,845,451 B2 | 12/2017 | Martin et al. | |
| 9,862,918 B2 | 1/2018 | Ito | |
| 9,933,373 B2 | 4/2018 | Vild et al. | |
| 10,067,065 B1 | 9/2018 | Alam et al. | |
| 10,254,274 B2 | 4/2019 | Miklas et al. | |
| 11,441,121 B2 | 9/2022 | Bennett et al. | |
| 11,613,722 B2 | 3/2023 | Martin et al. | |
| 2002/0022219 A1 | 2/2002 | Clements et al. | |
| 2002/0172621 A1 | 11/2002 | Barbera-Guillem | |
| 2003/0031829 A1 | 2/2003 | Tanner et al. | |
| 2003/0104494 A1 | 6/2003 | Ravkin et al. | |
| 2003/0183958 A1 | 10/2003 | Goff et al. | |
| 2003/0186217 A1 | 10/2003 | Bader | |
| 2003/0215941 A1 | 11/2003 | Campbell et al. | |
| 2004/0091397 A1 * | 5/2004 | Picard | B01L 3/50853 422/400 |
| 2004/0101955 A1 | 5/2004 | Whitley | |
| 2004/0125266 A1 | 7/2004 | Miyauchi et al. | |
| 2004/0216835 A1 | 11/2004 | Tanner et al. | |
| 2004/0259242 A1 | 12/2004 | Malinge et al. | |
| 2004/0259423 A1 | 12/2004 | Elbaz et al. | |
| 2005/0032208 A1 | 2/2005 | Oh et al. | |
| 2005/0047971 A1 | 3/2005 | Clements et al. | |
| 2005/0074873 A1 | 4/2005 | Shanler et al. | |
| 2005/0112030 A1 | 5/2005 | Gaus | |
| 2005/0116717 A1 | 6/2005 | Dransfield et al. | |
| 2005/0147959 A1 | 7/2005 | Frondoza et al. | |
| 2006/0110822 A1 | 5/2006 | Robbins et al. | |
| 2006/0234370 A1 | 10/2006 | Korpinen et al. | |
| 2006/0252044 A1 | 11/2006 | Okumura et al. | |
| 2006/0292654 A1 | 12/2006 | Reardon | |
| 2007/0178441 A1 | 8/2007 | Li | |
| 2007/0216897 A1 | 9/2007 | Sonda | |
| 2008/0003671 A1 | 1/2008 | Martin | |
| 2008/0009027 A1 | 1/2008 | Fraker et al. | |
| 2008/0118974 A1 | 5/2008 | Martin et al. | |
| 2008/0206857 A1 | 8/2008 | Kenney et al. | |
| 2008/0268515 A1 | 10/2008 | Cullimore et al. | |
| 2008/0297784 A1 | 12/2008 | Leblanc et al. | |
| 2008/0299649 A1 | 12/2008 | Martin et al. | |
| 2008/0300278 A1 | 12/2008 | Torrens Jover et al. | |
| 2009/0017540 A1 | 1/2009 | Nishio et al. | |
| 2009/0018033 A1 | 1/2009 | Morgan et al. | |
| 2009/0029462 A1 | 1/2009 | Beardsley et al. | |
| 2009/0037293 A1 | 2/2009 | Unger et al. | |
| 2009/0170190 A1 | 7/2009 | Nishi et al. | |
| 2009/0191620 A1 | 7/2009 | Martin et al. | |
| 2009/0288963 A1 | 11/2009 | Guerrieri et al. | |
| 2009/0298164 A1 | 12/2009 | Cattadoris et al. | |
| 2009/0298166 A1 | 12/2009 | Fang et al. | |
| 2010/0055774 A1 | 3/2010 | Wilson | |
| 2010/0068793 A1 | 3/2010 | Ungrin et al. | |
| 2010/0074515 A1 | 3/2010 | Zhao et al. | |
| 2010/0093075 A1 | 4/2010 | Muller | |
| 2010/0112014 A1 | 5/2010 | Gilbert et al. | |
| 2010/0112684 A1 | 5/2010 | Lee et al. | |
| 2010/0119418 A1 | 5/2010 | Clements et al. | |
| 2010/0170790 A1 | 7/2010 | Takahashi et al. | |
| 2010/0190197 A1 | 7/2010 | Martin et al. | |

(56) References Cited

U.S. PATENT DOCUMENTS

| | | |
|---|---|---|
| 2010/0197013 A1 | 8/2010 | Kamp et al. |
| 2010/0247386 A1 | 9/2010 | Deutsch et al. |
| 2010/0273258 A1 | 10/2010 | Lannutti et al. |
| 2010/0296084 A1 | 11/2010 | Berg et al. |
| 2010/0297600 A1 | 11/2010 | Cecchi |
| 2011/0086375 A1 | 4/2011 | Ungrin et al. |
| 2011/0097790 A1 | 4/2011 | Yerbic |
| 2011/0129923 A1 | 6/2011 | Wilson et al. |
| 2011/0229961 A1 | 9/2011 | Higashi et al. |
| 2012/0064627 A1 | 3/2012 | Khine et al. |
| 2012/0125936 A1* | 5/2012 | Byers ............... C12M 29/20 220/367.1 |
| 2012/0129208 A1 | 5/2012 | Khine et al. |
| 2012/0129257 A1 | 5/2012 | Yu et al. |
| 2012/0219572 A1 | 8/2012 | Prockop et al. |
| 2013/0052331 A1 | 2/2013 | Kram et al. |
| 2013/0122539 A1 | 5/2013 | Li et al. |
| 2013/0122580 A1 | 5/2013 | Tsukada et al. |
| 2013/0143254 A1 | 6/2013 | Thomas et al. |
| 2013/0164848 A1 | 6/2013 | Munaka et al. |
| 2013/0203159 A1* | 8/2013 | Itoh ............... C12M 23/10 435/299.1 |
| 2013/0344598 A1 | 12/2013 | Nistor |
| 2014/0004086 A1 | 1/2014 | Peak |
| 2014/0027784 A1 | 1/2014 | Wada et al. |
| 2014/0099717 A1 | 4/2014 | Fraker et al. |
| 2014/0106394 A1 | 4/2014 | Ko et al. |
| 2014/0106452 A1* | 4/2014 | Vukasinovic ....... C12N 5/0068 435/305.3 |
| 2014/0120573 A1 | 5/2014 | Tavana et al. |
| 2014/0178992 A1 | 6/2014 | Nakashima et al. |
| 2014/0221225 A1 | 8/2014 | Danen et al. |
| 2014/0226004 A1 | 8/2014 | Son et al. |
| 2014/0227784 A1 | 8/2014 | Ejiri et al. |
| 2014/0240489 A1 | 8/2014 | Furnas |
| 2014/0315296 A1 | 10/2014 | Wilson |
| 2014/0322806 A1 | 10/2014 | Bennett et al. |
| 2015/0004686 A1 | 1/2015 | Goral et al. |
| 2015/0064738 A1 | 3/2015 | Tsukada et al. |
| 2015/0072405 A1 | 3/2015 | Ito |
| 2015/0184119 A1 | 7/2015 | Tsukada et al. |
| 2015/0247112 A1 | 9/2015 | Orr et al. |
| 2016/0003796 A1 | 1/2016 | Kranbuehl |
| 2016/0017267 A1* | 1/2016 | Hansen ............... C12M 41/36 435/29 |
| 2016/0040120 A1 | 2/2016 | Gottwald et al. |
| 2016/0137962 A1* | 5/2016 | Ejiri ............... C12M 23/08 435/377 |
| 2016/0194588 A1 | 7/2016 | Guenat et al. |
| 2016/0216250 A1 | 7/2016 | Ritter et al. |
| 2016/0250631 A1 | 9/2016 | Kang et al. |
| 2017/0067009 A1 | 3/2017 | Sloane et al. |
| 2017/0067019 A1 | 3/2017 | Ho |
| 2017/0073625 A1 | 3/2017 | Kasuto et al. |
| 2017/0226455 A1 | 8/2017 | Fang et al. |
| 2017/0267959 A1 | 9/2017 | Martin et al. |
| 2017/0283757 A1 | 10/2017 | Carter et al. |
| 2017/0306281 A1* | 10/2017 | Martin ............... C12M 23/12 |
| 2017/0342363 A1 | 11/2017 | Fang et al. |
| 2018/0166743 A1 | 6/2018 | Lee et al. |
| 2018/0201888 A1 | 7/2018 | Miwa et al. |
| 2018/0301754 A1 | 10/2018 | Badding et al. |
| 2019/0006707 A1 | 1/2019 | Sakamoto et al. |
| 2019/0094208 A1* | 3/2019 | Vuong ............... C12M 21/08 |
| 2020/0064197 A1 | 2/2020 | Furnas |
| 2020/0131461 A1 | 4/2020 | Martin et al. |
| 2020/0199006 A1 | 6/2020 | Jain et al. |
| 2020/0239854 A1 | 7/2020 | Ayano et al. |
| 2021/0062126 A1* | 3/2021 | Martin ............... C12M 23/02 |
| 2022/0220434 A1 | 7/2022 | Martin et al. |
| 2022/0259540 A1 | 8/2022 | Li et al. |

FOREIGN PATENT DOCUMENTS

| | | |
|---|---|---|
| CA | 2679011 A1 | 9/2008 |
| CA | 2848875 A1 | 3/2013 |
| CN | 2186755 Y | 1/1995 |
| CN | 1168921 A | 12/1997 |
| CN | 1234112 A | 11/1999 |
| CN | 1867663 A | 11/2006 |
| CN | 1875093 A | 12/2006 |
| CN | 201626959 U | 11/2010 |
| CN | 101978041 A | 2/2011 |
| CN | 102105578 A | 6/2011 |
| CN | 102257123 A | 11/2011 |
| CN | 102449135 A | 5/2012 |
| CN | 102687023 A | 9/2012 |
| CN | 202450098 U | 9/2012 |
| CN | 202849407 U | 4/2013 |
| CN | 103080294 A | 5/2013 |
| CN | 103119151 A | 5/2013 |
| CN | 203513696 U | 4/2014 |
| CN | 103814125 A | 5/2014 |
| CN | 204608026 U | 9/2015 |
| CN | 204702760 U | 10/2015 |
| CN | 204714819 U | 10/2015 |
| CN | 204752742 U | 11/2015 |
| CN | 204803327 U | 11/2015 |
| CN | 205170866 U | 4/2016 |
| CN | 205669029 U | 11/2016 |
| CN | 205839030 U | 12/2016 |
| CN | 205990396 U | 3/2017 |
| CN | 107109340 A | 8/2017 |
| CN | 107109341 A | 8/2017 |
| CN | 107208025 A | 9/2017 |
| CN | 107460125 A | 12/2017 |
| DE | 8309876 U1 | 12/1983 |
| DE | 10019862 A1 | 11/2001 |
| DE | 202006017853 U1 | 2/2007 |
| DE | 102009005526 A1 | 7/2010 |
| DE | 102014214077 A1 | 1/2016 |
| DE | 102014017728 A1 | 6/2016 |
| EP | 307048 A2 | 3/1989 |
| EP | 0605527 A1 | 7/1994 |
| EP | 0681846 A2 | 11/1995 |
| EP | 0800571 A2 | 10/1997 |
| EP | 834552 A1 | 4/1998 |
| EP | 965633 A1 | 12/1999 |
| EP | 1181349 A1 | 2/2002 |
| EP | 1348533 A2 | 10/2003 |
| EP | 1445022 A2 | 8/2004 |
| EP | 1988152 A1 | 11/2008 |
| EP | 2032262 A2 | 3/2009 |
| EP | 2617807 A1 | 7/2013 |
| EP | 2653531 A1 | 10/2013 |
| EP | 2759592 A1 | 7/2014 |
| EP | 2896684 A1 | 7/2015 |
| EP | 3081627 A1 | 10/2016 |
| EP | 3296018 A1 | 3/2018 |
| EP | 3351615 A1 | 7/2018 |
| EP | 3372666 A1 | 9/2018 |
| GB | 2147100 A | 5/1985 |
| JP | 03-139350 A | 6/1991 |
| JP | 06-038734 A | 2/1994 |
| JP | 06327462 A | 11/1994 |
| JP | 09173049 A | 7/1997 |
| JP | 09-234811 A | 9/1997 |
| JP | 10210866 A | 8/1998 |
| JP | 10210966 A | 8/1998 |
| JP | 2001-106749 A | 4/2001 |
| JP | 2003135056 A | 5/2003 |
| JP | 2003180335 A | 7/2003 |
| JP | 2004129558 A | 4/2004 |
| JP | 2004-535829 A | 12/2004 |
| JP | 2005-080660 A | 3/2005 |
| JP | 2006-121991 A | 5/2006 |
| JP | 2006-191809 A | 7/2006 |
| JP | 2007-510429 A | 4/2007 |
| JP | 3139350 U | 2/2008 |
| JP | 2009-017810 A | 1/2009 |
| JP | 2009050194 A | 3/2009 |

(56) References Cited

FOREIGN PATENT DOCUMENTS

| | | |
|---|---|---|
| JP | 2009-183288 A | 8/2009 |
| JP | 2009-542230 A | 12/2009 |
| JP | 2010088347 A | 4/2010 |
| JP | 2010104327 A | 5/2010 |
| JP | 2010-518879 A | 6/2010 |
| JP | 2010158214 A | 7/2010 |
| JP | 2011-509686 A | 3/2011 |
| JP | 2011-521642 A | 7/2011 |
| JP | 2011172533 A | 9/2011 |
| JP | 2011-528226 A | 11/2011 |
| JP | 2012249547 A | 12/2012 |
| JP | 2013055911 A | 3/2013 |
| JP | 2014132869 A | 7/2014 |
| JP | 2015012827 A | 1/2015 |
| JP | 2015-029431 A | 2/2015 |
| JP | 2015073520 A | 4/2015 |
| JP | 2016-002023 A | 1/2016 |
| JP | 5845185 B2 | 1/2016 |
| JP | 2016-093149 A | 5/2016 |
| JP | 2016-136920 A | 8/2016 |
| JP | 2016136921 A | 8/2016 |
| JP | 2017-532970 A | 11/2017 |
| JP | 2018-108032 A | 7/2018 |
| KR | 1020140113139 A | 9/2014 |
| KR | 10-2014-0125662 A | 10/2014 |
| KR | 10-2017-0008539 A | 1/2017 |
| KR | 102460969 * | 10/2022 |
| WO | 1992007063 A2 | 4/1992 |
| WO | 93/07258 A1 | 4/1993 |
| WO | 96/21851 A2 | 7/1996 |
| WO | 9815355 A2 | 4/1998 |
| WO | 1998031466 A1 | 7/1998 |
| WO | 2001080997 A1 | 11/2001 |
| WO | 2001092462 A1 | 12/2001 |
| WO | 2004/044120 A2 | 5/2004 |
| WO | 2004/094060 A1 | 11/2004 |
| WO | 2005047464 A2 | 5/2005 |
| WO | 2006043267 A1 | 4/2006 |
| WO | 2007/015770 A1 | 2/2007 |
| WO | 2007097120 A1 | 8/2007 |
| WO | 2008/006104 A2 | 1/2008 |
| WO | 2008/008149 A2 | 1/2008 |
| WO | 2008/106771 A1 | 9/2008 |
| WO | 2008118500 A1 | 10/2008 |
| WO | 2008/140295 A1 | 11/2008 |
| WO | 2008/149039 A2 | 12/2008 |
| WO | 2008153783 A1 | 12/2008 |
| WO | 2009094125 A2 | 7/2009 |
| WO | 2009148509 A1 | 12/2009 |
| WO | 2009148512 A2 | 12/2009 |
| WO | 2010008566 A2 | 1/2010 |
| WO | 2010/042072 A1 | 4/2010 |
| WO | 2010/069589 A1 | 6/2010 |
| WO | 2012036011 A1 | 3/2012 |
| WO | 2012/077683 A1 | 6/2012 |
| WO | 2012170232 A1 | 12/2012 |
| WO | 2013042360 A1 | 3/2013 |
| WO | 2013/108293 A1 | 7/2013 |
| WO | 2013/116449 A1 | 8/2013 |
| WO | 2014/042162 A1 | 3/2014 |
| WO | 2014072432 A1 | 5/2014 |
| WO | 2014/140181 A1 | 9/2014 |
| WO | 2014156455 A1 | 10/2014 |
| WO | 2014165273 A1 | 10/2014 |
| WO | 2014171782 A1 | 10/2014 |
| WO | 2014/179196 A1 | 11/2014 |
| WO | 2014196204 A1 | 12/2014 |
| WO | 2015033507 A1 | 3/2015 |
| WO | 2015/061907 A1 | 5/2015 |
| WO | 2015/087369 A1 | 6/2015 |
| WO | 2016/020992 A1 | 2/2016 |
| WO | 2016064757 A1 | 4/2016 |
| WO | 2016069885 A1 | 5/2016 |
| WO | 2016069892 A1 | 5/2016 |
| WO | 2016069895 A1 | 5/2016 |
| WO | 2016069917 A1 | 5/2016 |
| WO | 2016069930 A1 | 5/2016 |
| WO | 2016/157322 A1 | 10/2016 |
| WO | 2017025584 A1 | 2/2017 |
| WO | 2017/047735 A1 | 3/2017 |
| WO | 2017/077163 A1 | 5/2017 |
| WO | 2017142410 A1 | 8/2017 |
| WO | 2018/068034 A1 | 4/2018 |
| WO | 2018200893 A1 | 11/2018 |
| WO | 2019/010401 A1 | 1/2019 |
| WO | 2019014621 A1 | 1/2019 |
| WO | 2019014627 A1 | 1/2019 |
| WO | 2019014635 A1 | 1/2019 |
| WO | 2019014636 A1 | 1/2019 |
| WO | 2019178039 A1 | 9/2019 |

OTHER PUBLICATIONS

Alepee et al, "State-Of-The-Art 3D Cultures (Organs-On-A-Chip) in Safety Testing and Pathophysiology"; Transatlantic Think Tank for Toxicology, T4 Workshop Report, Altex 31, Apr. 2014, pp. 441-477, Retrieved From: http://dx.doi.org/10.14573/altex1406111 (Jul. 14, 2014).

Aline, "We Engineer Microfluidic Products" ; 7 Pages; (2020) https://alineinc.com/.

G-Plate: Accelerate your cell cultures to the next dimension, "An original cell culture model allowing for island-shaped 3D cell aggregates", 1 page, retrieved Sep. 8, 2015.

Anada et al, "An Oxygen-Permeable Spheroid Culture System for the Prevention of Central Hypoxia and Necrosis of Spheroids"; Biomaterials 33 (2012) 8430-8441.

Bartosh et al, "Aggregation of Human Mesenchymal Stromal Cells (MSCS) Into 3D Spheroids Enhances Their Antiinflammatory Properties"; PNAS, Aug. 3, 2010, 107(31):13724-13729.

BIOIVT Elevating Science®; 6 Pages; (2020); http://www.hepregen.com/.

Carver et al, "Multicellular Tumor Spheroids as a Model for Assessing Delivery of Oligonucleotides in Three Dimensions"; Molecular Therapy-Nucleic Acids (2014) 3, E153; 8 Pages.

Chen et al, "Microfluidic array for three-dimensional perfusion culture of human mammary epithelial cells"; Biomedical Microdevices, 2011, 13(4):753-758.

Cheng et al, "MICRORNA-34a Targets Forkhead Box J2 To Modulate Differentiation of Endothelial Progenitor Cells in Response to Shear Stress", J Mol Cell Cardiol. 74 (2014) 4-12.

Choi et al, "Feasibility of a simple double-layered coculture system incorporating metabolic processes of the intestine and liver tissue: application to the analysis of benzo[a]pyrene toxicity", Toxicology in Vitro 18 (2004) 393-402.

CN-BIO, "Transforming Drug Discovery and the Lives of Patients"; 5 Pages; (2020) http://cn-bio.com/.

Colazzo et al, "Shear Stress and Vegf Enhance Endothelial Differentiation of Human Adipose-Derived Stem Cells", Growth Factors, 2014, 32(5):139-149.

CORNING® HTS TRANSWELL®—96 Tissue Culture Systems, Permeable Supports for High Throughput Screening Applications; 2 Pages (2004).

Tissue Dynamics, "Disruptive Drug Development"; 3 Pages; (Downloaded Mar. 9, 2020); https://www.tissuedynamics.com/.

Dolznig et al, "Organotypic spheroid cultures to study tumor-stroma interaction during cancer development", Drug Discovery Today: Disease Models, 2011, 8(2-3):113-118.

Domansky et al, "Perfused Multiwell Plate for 3D Liver Tissue Engineering", Lab Chip, 2010, 10:51-58.

Emulate, 6 Pages; (2019) https://emulatebio.com/.

Tissue, "Emulating Human Biology, Pioneering Human-On-A-Chip Developments"; 1 Page; (Downloaded Mar. 9, 2020) https://www.tissuse.com/en/.

Endo et al, "Gene transfection to spheroid culture system on micropatterned culture plate by polyplex nanomicelle: a novel platform of genetically-modified cell transplantation", Drug Deliv. and Transl. Res., 2012, 2:398-405.

(56) References Cited

OTHER PUBLICATIONS

Engelberg et al, "Essential operating principles for tumor spheroid growth", BMC Systems Biology 2008, 2:110, 19 pages.
Friedrich et al, "Experimental anti-tumor therapy in 3-D: spheroids—old hat or new challenge?" Int J Radiat Biol 2007, 83(11-12):849-871.
Friedrich et al, "Spheroid-based drug screen: considerations and practical approach", Nature protocols, 2009, 4(3):309-323.
Frith et al, "Dynamic three-dimensional culture methods enhance mesenchymal stem cell properties and increase therapeutic potential", Tissue engineering, 2010, 16(4):735-749.
Fukuda et al, "Efficacy of a polyurethane foam/spheroid artificial liver by using human hepatoblastoma cell line (Hep G2)", Cell Transplantation, 2003, 12:51-58.
GeoCHEM Incorporated, Product Line; https://www.geocheminc.com, 4 Pages; (2020).
Haycock, "3D cell culture: a review of current approaches and techniques", Methods Mol Biol, 2011; 695:1-15.
Hirschhaeuser et al, "Multicellular tumor spheroids: An underestimated tool is catching up again", Journal of Biotechnology 148 (2010) 3-15.
Howes et al, "3-Dimensional Culture Systems for Anti-Cancer Compound Profiling and High-Throughput Screening Reveal Increases in EGFR Inhibitor-Mediated Cytotoxicity Compared to Monolayer Culture Systems"; PLOS ONE; Sep. 2004, 9(9), 11 Pages.
Hiribar et al, "Nonlinear 3D Projection Printing of Concave Hydrogel Microstructures for Long-Term Multicellular Spheroid and Embryoid Body Culture"; Lab Chip, 2015, 15, 2412-2418.
Hwang et al, "Microwell-Mediated Control of Embryoid Body Size Regulates Embryonic Stem Cell Fate via Differential Expression of WNT5A and WNT11"; PNAS, 2009, 106(40):16978-16983.
HμREL® Corporation, Bioanalytic Tools Company; 2 Pages; (2013); http://hurelcorp.com/.
Jeon et al, "Combined Effects of Flow-Induced Shear Stress and Micropatterned Surface Morphology on Neuronal Differentiation of Human Mesenchymal Stem Cells" J Biosci Bioeng, 2014, 117(2):242-247.
Jiang et al, "Shear Enhances Thrombopoiesis and Formation of Microparticles That Induce Megakaryocytic Differentiation of Stem Cells", Blood, Sep. 25, 2014; 124(13):2094-2103.
Kelm et al, "Method for generation of homogeneous multicellular tumor spheroids applicable to a wide variety of cell types", Biotechnology and Bioengineering 2003; 83(2):173-180.
Kim et al, "Shear Stress Induced by an Interstitial Level of Slow Flow Increases the Osteogenic Differentiation of Mesenchymal Stem Cells Through TAZ Activation" PLoS ONE, Mar. 21, 2014; 9(3), e92427, 9 pages.
Koide et al, "Formation of multicellular spheroids composed of adult rat hepatocytes in dishes with positively charged surfaces and under other nonadherent environments", Exp Cell Res 1990; 186:227-235.
Kunz-Schughart et al, "The use of 3-D cultures for high-throughput screening: the multicellular spheroid model", J Biomol Screen 2004, 9(4):273-285.
Kutsuzawa et al, "Highly Robust Protein Production by Co-Culture of CHO Spheroids Layered on Feeder Cells in Serum-Free Medium"; Colloid Polym Sci (2014) 292; 839-848.
Labusca, "Scaffold free 3D culture of mesenchymal stem cells; implications for regenerative medicine", J Transplant Stem Cel Biol 2015 2(1): 8.
Landry et al, "Spheroidal aggregate culture of rat liver cells: histotypic reorganization, biomatrix deposition, and maintenance of functional activities" J Cell Biol 1985; 101:914-923.
Lau et al, "Evaluation of a Novel in Vitro CACO-2 Hepatocyte Hybrid System for Predicting in Vivo Oral Bioavailability" Drug Metabolism and Disposition, vol. 32, No. 9, pp. 937-942, 2004.
Liquid Surge Control, LLC; "The Latest in Drop-In Baffle Technology"; 2 Pages; (2019).

Liu et al, "Quasi-spherical microwells on superhydrophobic substrates for long term culture of multicellular spheroids and high throughput assays" Biomaterials 35 (2014) pp. 6060-6068.
Liu et al, "Advanced Micromachining of Concave Microwells for Long Term On-Chip Culture of Multicellular Tumor Spheroids", ACS Appl. Mater. Interfaces, 2014, 6, 8090-8097.
Lu et al, "Galactosylated PVDF membrane promotes hepatocyte attachment and functional maintenance" Biomaterials 24 (2003) 4893-4903.
Markovitz-Bishitz, "A polymer microstructure array for the formation, culturing, and high throughput drug screening of breast cancer spheroids" Biomaterials 31 (2010) 8436-8444.
Messner et al, Multi-cell type human liver microtissues for hepatotoxicity testing. Archives of Toxicology, Nov. 11, 2012, 5 pages.
ELVEFLOW; "Microfluidics Innovation Center"; 6 Pages; (Downloaded Mar. 9, 2020); https://www.elveflow.com/.
Mironov et al, "Organ Printing: Tissue Spheroids as Buliding Blocks" Biomaterials, 2009; 30(12): 2164-2174.
Moon et al, "Optimizing Human Embryonic Stem Cells Differentiation Efficiency by Screening Size-Tunable Homogenous Embryoid Bodies" ; Biomaterials; 35 (2014) 5987-5997.
Urich et al, "Multicellular Self-Assembled Spheroidal Model of the Blood Brain Barrier"; Scientific Reports, 3, 1500, 8 Pages.
Murphy et al, "3D Bioprinting of Tissues and Organs" ; Nature Biotechnology, vol. 32, No. 8, Aug. 2014, pp. 773-785.
Nortis; "Bridging the Gap Between In Vitro and In Vivo Research" ; 16 Pages; (2015); https://www.nortisbio.com/.
Mimetas the Organ-On-A-Chip Company; "Organ-On-A-Chip Models for Science and Pharma"; 4 Pages; (Downloaded Mar. 9, 2020); https://mimetas.com/.
Otsuka et al, "Two-dimensional multiarray formation of hepatocyte spheroids on a microfabricated PEG-brush surface." ChemBioChem 2004; 5:850-855.
Peshwa et al, "Mechanistics of formation and ultrastructural evaluation of hepatocyte spheroids." In Vitro Cell Dev Biol Anim 1996; 32:197-203.
Organovo, "Pioneering Bioprinted Tissues to Treat Disease"; 2 Pages; (Downloaded Mar. 9, 2020) http://organovo.com/.
Rezende et al, "Scalable Biofabrication of Tissue Spheroids for Organ Printing"; Sciverse Science Direct, Procedia CIRP 5, (2013) 276-281.
Sa et al, "Round-bottomed Honeycomb Microwells: Embryoid body shape correlates with stem cell fate" Journal of Developmental Biology and Tissue Engineering vol. 4(2), pp. 12-22, May 2012.
Sakai et al, "Large-scale preparation and function of porcine hepatocyte spheroids." Int J Artif Organs 1996; vol. 19, No. 5, pp. 294-301.
Sakai et al, "Detachably Assembled Microfluidic Device for Perfusion Culture and Post-Culture Analysis of Spheroid Array" ; Biotechnol. J. 2014, 9, 971-979.
Sakai et al, "Technique for the Control of Spheroid Diameter Using Microfabricated Chips"; ScienceDirect, ACTA Biomaterialia 3 (2007) 1033-1040.
Sart et al, "Three-dimensional aggregates of mesenchymal stem cells: cellular mechanisms, biological properties and applications" Tissue engineering, 2013, Part B, vol. 00, No. 00, 1-16.
Satoh et al, "A Pneumatic Pressure-Driven Multi-Throughput Microfluidic Circulation Culture System" Lab Chip, 2016, 16, 2339-2348.
Seldon et al, "Evaluation of Encapsulated Liver Cell Spheroids in a Fluidised-Bed Bioartificial Liver for Treatment of Ischaemic Acute Liver Failure in Pigs in a Translational Setting"; PLOS ONE, 2013, 8(12), e82312.
Takezawa et al, "Morphological and immuno-cytochemical characterization of a hetero-spheroid composed of fibroblasts and hepatocytes" J Cell Sci 1992; 101:495-501.
Tara; "Innovating Predictive Cardiac Physiology" ; 4 Pages; (2019) http://tarabiosystems.com/.
The Lab Depot® Products for Discovery Lab Supplies; Shake Flasks, 3 and 4 Baffles Product Information; 5 Pages (2019).
Tobe et al, "Receptor-mediated formation of multilayer aggregates of primary cultured adult rat hepatocytes on lactose-substituted polystyrene" Biochem Biophys Res Commun 1992; 184(1):225-230.

(56) References Cited

OTHER PUBLICATIONS

Tong et al, "Long-term culture of adult rat hepatocyte spheroids." Exp Cell Res 1992; 200:326-332.
Truckenmuller et al, Thermoforming of Film-Based Biomedical Microdevices, Adv. Mater. 2011, 23, pp. 1311-1329.
Tung et al, "High-throughput 3D spheroid culture and drug testing using 384 hanging drop array" Analyst, 2011, 136(3), 473-478.
Uchida et al, "An Injectable Spheroid System With Genetic Modification for Cell Transplantation Therapy"; Biomaterials, 35 (2014) 2499-2506.
Vinci et al, Advances in establishment and analysis of three-dimensional tumor spheroid-based functional assays for target validation and drug evaluation, BMC Biology 2012, 10:29.
Weegman et al, "Nutrient Regulation by Continuous Feeding Removes Limitations on Cell Yield in the Large-Scale Expansion of Mammalian Cell Spheroids"; PLOS ONE, 2013, vol. 8, Issue 10, e76611, 10 Pages.
Wikipedia, "Antiroll Tanks"; 3 Pages; Page Last Edited May 23, 2019.
Wrighton et al, "Forces of Change: Mechanics Underlying Formation of Functional 3D Organ Buds" Cell Stem Cell, May 7, 2015; 16(5): 453-454.
Xu et al, "Characterisation of some cytotoxic endpoints using rat liver and HepG2 spheroids as in vitro models and their application in hepatotoxicity studies. I. Glucose metabolism and enzyme release as cytotoxic markers." Toxicol Appl Pharmacol 2003;189:100-111.
Yamada et al, "Efficient induction of hepatocyte spheroids in a suspension culture using a water-soluble synthetic polymer as an artificial matrix." J Biochem 1998; 123:1017-1023.
AxoSIM, Nerve-On-A-Chip Mini-Brain About Team; 6 Pages; (Downloaded Mar. 9, 2020); http://axosim.com/.
Corning Life Sciences Product Portfolio; 5 Pages Saved Mar. 6, 2020.
Madoux et al, "Building Phenotypic 3D Spheroid HTS Assays to Identify Synthetic Lethal Small Molecule Inhibitors of KRAS"; the Scripps Research Institute Molecular Screening Center and Department of Cancer Biology, Scripps Florida, Jupiter, Florida, Department of Pathology, Jupiter Medical Center, Jupiter, Florida.
Stemcell Technologies, Reproducible and Uniform Embryoid Bodies Using AggreWell Plates, StemCell Technologies, Technical Manual Version 3.0.0, Mar. 2011, Catalog #29146, pp. 1-28.
Lovett et al. "Vascularization Strategies for Tissue Engineering" Tissue Engineering Part B, 2009, vol. 15, No. 3, pp. 353-370.
"Identification grid for microplates", Rtreived from: https://www.kisker-biotech.com/frontoffice/product?produitId=0N-27-11, 2 pages, 2021.
"Laboratory Flasks Selection Guide: Types, Features, Applications", Engineering360, <https://www.globalspec.com/learnmore/labware_scientific_instruments/labware_consumables/laboratory_flasks#:~:text=Laboratory%20flasks%20are%20lab%20vessels,the%20opening%20at%20the%20neck.> accessed Apr. 8, 2022 (Year: 2022).

Achilli et al., "Advances in the Formation, Use and Understanding of Multi-cellular Spheroids", Expert Opinion on Biological Therapy, vol. 12, No. 10, Jul. 2012, pp. 1347-1360.
Brandrup et al., "Polymer Handbook", Fourth Edition, Wiley-Interscience Publication, , Permeability and diffusion data, 1999, 9 pages (Contributors; Preface).
Chinese Patent Application No. 201880051225.6, Office Action, dated Feb. 13, 2023, 4 pages Chinese Patent Office.
Curcio et al. "Mass transfer and metabolic reactions in hepatocyte spheroids cultured in rotating wall gas-permeable membrane system." Biomaterials 28 (2007) 5487-5497. (Year: 2007).
Endo et al., "Gene transfection to spheroid culture system on micropatterned culture plate by polyplex nanomicelle: a novel platform of genetically-modified cell transplantation", Drug Deliv. and Transl. Res., 2012, vol. 2, p. 398-405.
Evenou et al. "Spontaneous Formation of Highly Functional Three-Dimensional Multilayer from Human Hepatoma Hep G2 Cells Cultured on an Oxygen-Permeable Polydimethylsiloxane Membrane." Tissue Engineering: Part C vol. 16, No. 2, 2010, pp. 311-318. (Year: 2010).
Hsiao et al., "Effects of 3D Microwell Culture on Initial Fate Specification in Human Embryonic Stem Cells", Published in final edited form as AIChE J. vol. 60 No.4, Apr. 2014, pp. 1225-1235.
Huang et al., "Preparation of dense Ta-LLZO/MgO composite Li-ion solid electrolyte: Sintering, microstructure, performance and the role of MgO", Journal of Energy Chemistry, vol. 39, 2019, pp. 8-16.
Junji Fukuda et al., "Hepatocyte Spheroid Arrays Inside Microwells Connected With Microchannels", BIOMICROFLUIDICS 5, 2011, pp. 10.
Koike et al. "Characterization of Embryo id Bodies of Mouse Embryonic Stem Cells Formed under Various Culture Conditions and Estimation of Differentiation Status of Such Bodies." Journal of Bioscience and Bioengineering vol. I 04, No. 4, 294-299. 2007. (Year: 2007).
Lin et al., "La2Zr2O7 and MgO co-doped composite Li-Garnet solid electrolyte", Journal of Energy Chemistry, vol. 40, 2020, pp. 132-136.
LONZA Inc., "SeaPrep Agarose: An Ultralow Gelling, Soft Agarose", Available Online at <http://www.lonzabio.jp/catalog/pdf/pd/PD031.pdf>, 2007, pp. 1-4.
Martin et al., "Agarose and Methylcellulose Hydrogel Blends for Nerve Regeneration Applications", J. Neural Eng., vol. 5, 2008, pp. 221-231.
McMillan, "Shear stress in microfluidic devices" Darwin Microfludics interner article (Year: 2017).
Polyimide: Japan Polyimide and Aromatic Polymers Study Group, 2010, pp. 364-371 Table 2.
Yang et al., "An Agarose-Gel Based Method for Transporting Cell Lines", Current Chemical Genomics, vol. 3, Jan. 2009, pp. 50-53.
Zuidema et al., "Fabrication and Characterization of Tunable Polysaccharide Hydrogel Blends for Neural Repair", Acta Biomaterialia, vol. 7, No. 4, Apr. 2011, pp. 1634-1643.

* cited by examiner

MICROCAVITY DISHES WITH SIDEWALL INCLUDING LIQUID MEDIUM DELIVERY SURFACE

This application claims the benefit of priority under 35 U.S.C. § 365 of International Patent Application Serial No. PCT/US2018/041985 filed on Jul. 13, 2018, the content of which is relied upon and incorporated herein by reference in its entirety.

BACKGROUND

Field

The present specification generally relates to cell culture devices, and more specifically, to microcavity dishes with sidewalls that include liquid medium delivery surfaces.

Technical Background

Cell culture dishes (e.g., a "Petri dish") are used for culturing of cells and microbes. The cell culture dishes may come in a variety of sizes, and can be round or rectangular. The cell culture dishes may have a flat floor suitable for two-dimensional cell cultures. Accordingly, this creates an environment for the cells to be grown in as the cells attach to the planar floor of the cell culture dishes and spread uniformly along the flat dish.

In contrast, cells grown in three-dimensional cell cultures are able to attach to other deposited cells within the three-dimensional environment thereby forming spheroids, creating a more natural interaction between the cells. This native arrangement of cells provides a flexible configuration, similar to that of natural tissues. Providing an accurate exemplification of a tissue microenvironment is desirable when conducting experimental research for developing therapies against diseases to increase accuracy. Since cells do not grow in two-dimensions within a human body, it may be desirable to develop these therapies in a three-dimensional culture that more closely resembles the natural environment.

Culturing cells as spheroids in a microcavity substrate can require some specific characteristics in the cell culture dishes. Activities that create turbulence in the culture media (e.g., aspiration) can cause the spheroids to be lifted out of their microcavities and cause movement into another microcavity. If there are multiple spheroids in a single microcavity, the spheroids may join together, forming a much larger spheroid than other spheroids. It may be desirable to have spheroids of the same size for certain applications from high throughput screening to cell therapy.

Accordingly, a need exists for a microcavity dish having built-in liquid medium handling features that can discourage turbulence in the culture media.

SUMMARY

According to one embodiment, a microcavity dish for cultivating cells includes a dish body including a sidewall that encloses a cell culture chamber within the dish body. The dish body has a top and a bottom. The bottom includes a cell culturing substrate comprising an array of microcavities. The sidewall includes a transition portion that divides the sidewall into an upper portion and a lower portion that is offset inward relative to the upper portion defining a liquid medium delivery surface that extends at least partially along an interior surface of the sidewall and slopes toward the bottom.

In another embodiment, a microcavity dish for cultivating cells includes a dish body including a sidewall that encloses a cell culture chamber within the dish body. The dish body has a top and a bottom. The bottom includes a cell culturing substrate comprising an array of microcavities. A liquid delivery track extends along the sidewall and at least partially along the cell culture chamber defining a liquid medium delivery surface. The liquid delivery track has a first end nearer the top than the bottom of the dish body and an opposite second end nearer the bottom than the top of the dish body.

In another embodiment, a method of forming a microcavity dish for cultivating cells is provided. The method includes filling a mold with a molten plastic material. A dish body is removed from the mold. The dish body includes a sidewall that encloses a cell culture chamber within the dish body. The dish body has a top and a bottom, and the sidewall includes a transition portion that divides the sidewall into an upper portion and a lower portion that is offset inward relative to the upper portion defining a liquid medium delivery surface that extends at least partially along an interior surface of the sidewall and slopes toward the bottom.

Additional features and advantages of the microplate apparatus and fluidic device described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
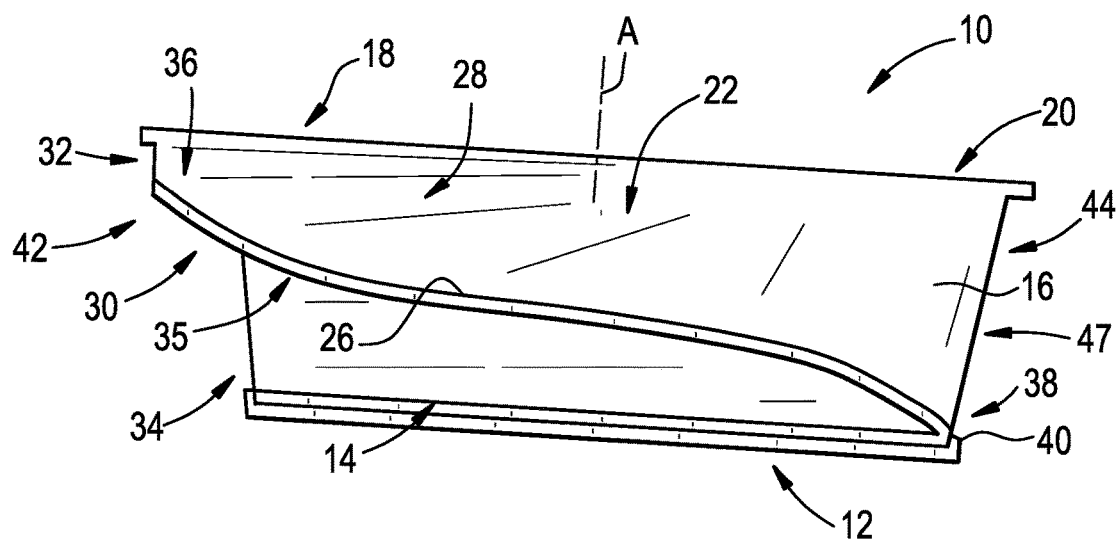
FIG. 1 is a diagrammatic side view of a microcavity dish including liquid medium delivery surface, according to one or more embodiments shown and described herein.

Reference will now be made in detail to various embodiments of microcavity dishes with sidewalls that include liquid medium delivery surfaces, examples of which are illustrated in the accompanying drawings. Whenever possible, the same reference numerals will be used throughout the drawings to refer to the same or like parts. Directional terms as used herein—for example up, down, right, left, front, back, top, bottom, distal, and proximal—are made only with reference to the figures as drawn and are not intended to imply absolute orientation.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used herein, the singular forms "a," "an" and "the" include plural referents unless the context clearly dictates otherwise. Thus, for example, reference to "a" component includes aspects having two or more such components, unless the context clearly indicates otherwise.

Embodiments described herein are directed to microcavity dishes that include a cell culturing substrate with an array of micron-sized wells that promote formation of spheroids. Spheroids are three-dimensional aggregates of cells, which can more closely resemble the natural cell environment compared with two-dimensional cell cultures. To avoid creating turbulence when aspirating and dispensing medium, the microcavity dishes incorporate a liquid medium delivery surface that is provided by a ramp-like structural feature that extends along an inner surface of a sidewall of the microcavity dishes. The microcavity dishes may further include a lid that can engage an upper edge of the sidewall and form a seal therewith. In some embodiments, the sidewall and lid may include cooperating mating structures, such as threads that engage one another to close the lid against the sidewall.

Referring to FIG. 1, a microcavity dish 10 is illustrated that includes a bottom 12 that includes a cell culturing substrate 14 and a sidewall 16 that extends outwardly from the bottom 12 to a top edge 18. The sidewall 16 and the bottom 12 form a dish body 20. In the illustrated embodiment, the sidewall 16 is round (e.g., circular) and the dish body 20 partially encloses a cell culture chamber 22. The sidewall 16 may be formed of any suitable material and can be optically transparent, such as a thermoformable polymer material. In some embodiments, the cell culturing substrate 14 may be formed separately from the sidewall 16 and be connected thereto. In other embodiments, the cell culturing substrate 14 may be formed integrally with the sidewall 16. The cell culturing substrate 14, for example, may be formed of a porous plastic material, for example.

The microcavity dish 10 includes a liquid medium delivery surface 26 that extends along an interior surface 28 (inner circumference) of the sidewall 16. In the example of FIG. 1, the liquid medium delivery surface 26 is defined by a transition portion 30 of the sidewall 16 that provides a liquid delivery track 35 and divides the sidewall 16 into an upper portion 32 and a lower portion 34 that is offset inward toward a central axis A of the dish body 20 relative to the upper portion 32. In these embodiments, the transition portion 30 may be formed as a monolithic part of the sidewall 16 (e.g., using a molding process). Forming the lower portion 34 smaller in outer dimension than the upper portion 32 can facilitate release of the dish body 20 from a mold.

The transition portion 30 and its liquid medium delivery surface 26 has a first end 36 that is near to the top edge 18 and an opposite, second end 38 that is near to a bottom edge 40 of the sidewall 16. The first end 36 may be at one side 42 of the sidewall 16 and the second end 38 may be at an opposite side 44 of the sidewall 16 depending on a length of the transition portion 30. In some embodiments, such as the one illustrated, the transition portion 30 extends only partially around the interior surface 28 such that a portion 47 of the sidewall 16 is straight vertically and does not include the transition portion 30.

The transition portion 30 extends from the first end 36 toward the second end 38 on a decline. In some embodiments, the slope of the decline of the transition portion 30 may change between the first end 36 and the second end 38. In some embodiments, the slope of the decline of the transition portion 30 may be substantially constant between the first end 36 and the second end 38 or a combination of constant and changing slopes along different segments of the transition portion 30.

Figure 2:
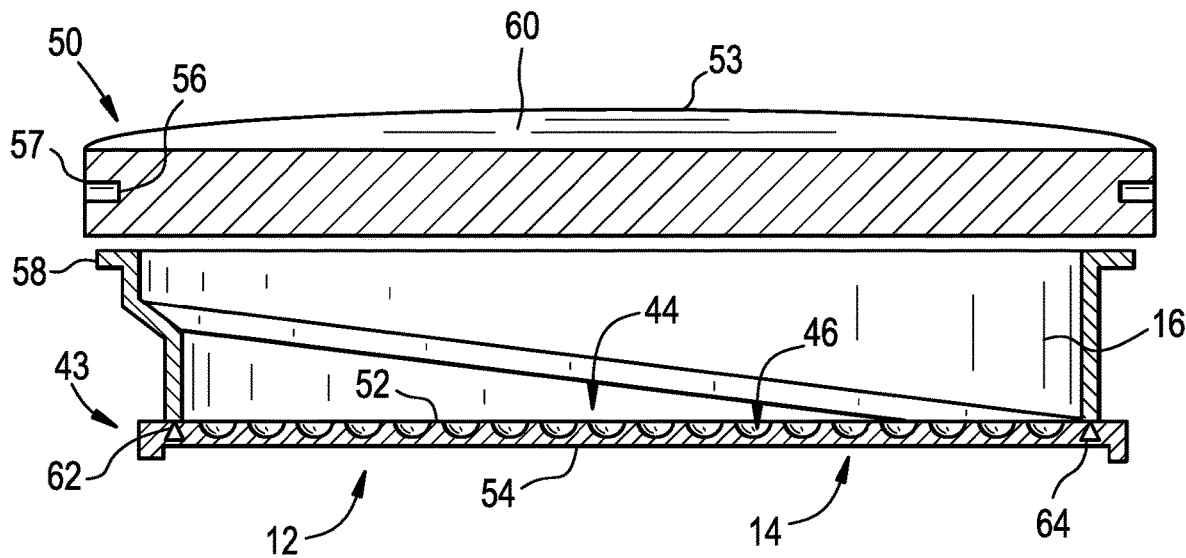
FIG. 2 is a diagrammatic side sectional view of the microcavity dish of FIG. 1, according to one or more embodiments shown and described herein.
Figure 3:
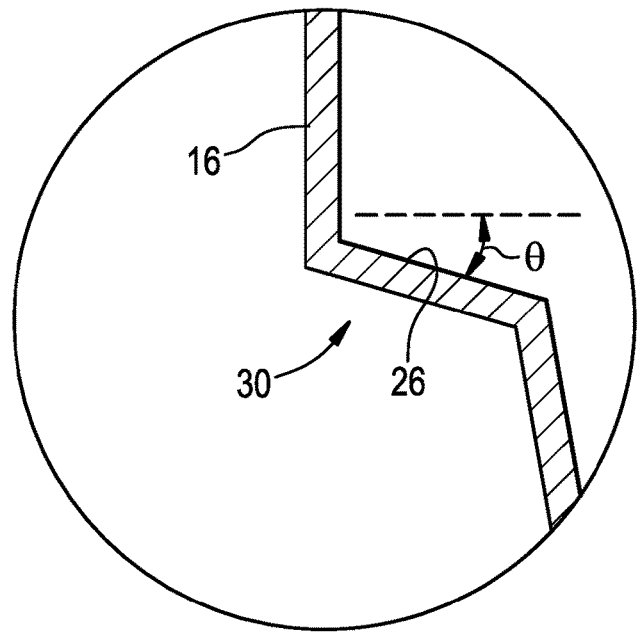
FIG. 3 is a diagrammatic detail view of a transition portion including the liquid medium delivery surface of the microcavity dish, according to one or more embodiments shown and described herein.

FIG. 2 illustrates a diagrammatic cross-section view of the microcavity dish 10 including the sidewall 16, the upper portion 32 and the lower portion 34 with the transition portion 30 located therebetween. Referring also to FIG. 3, the transition portion 30 includes the liquid medium delivery surface 26 that, in some embodiments, extends at an angle θ to horizontal. That is, the liquid medium delivery surface 26 may be sloped from the sidewall 16 downward toward the bottom 12. In other embodiments, the liquid medium delivery surface 26 may be horizontal.

Referring again to FIG. 2, the bottom 12 includes the cell culturing substrate 14. In some embodiments, the sidewall 16 may include an outwardly extending flange portion 43 that can be used to receive an outer periphery 42 of the cell culturing substrate 14 for connection to the sidewall 16. Energy directors 62 and 64 may be used to connect the cell culturing substrate 14 and the sidewall 16. The energy directors 62 can be used to absorb shock when the microcavity dish 10 is being handled, for example. In some embodiments, the outer periphery 42 of the cell culturing substrate 14 is flat, while a central cell culturing region 44 within the outer periphery 42 includes microcavities 46 that are positioned side-by-side over the area of the cell culturing region 44. The microcavities 46 may be formed as recesses in an interior surface 52 of the cell culturing substrate 14. The microcavities 46 extend from the interior surface 52 toward an exterior surface 54 of the cell culturing substrate 14.

Figure 4:
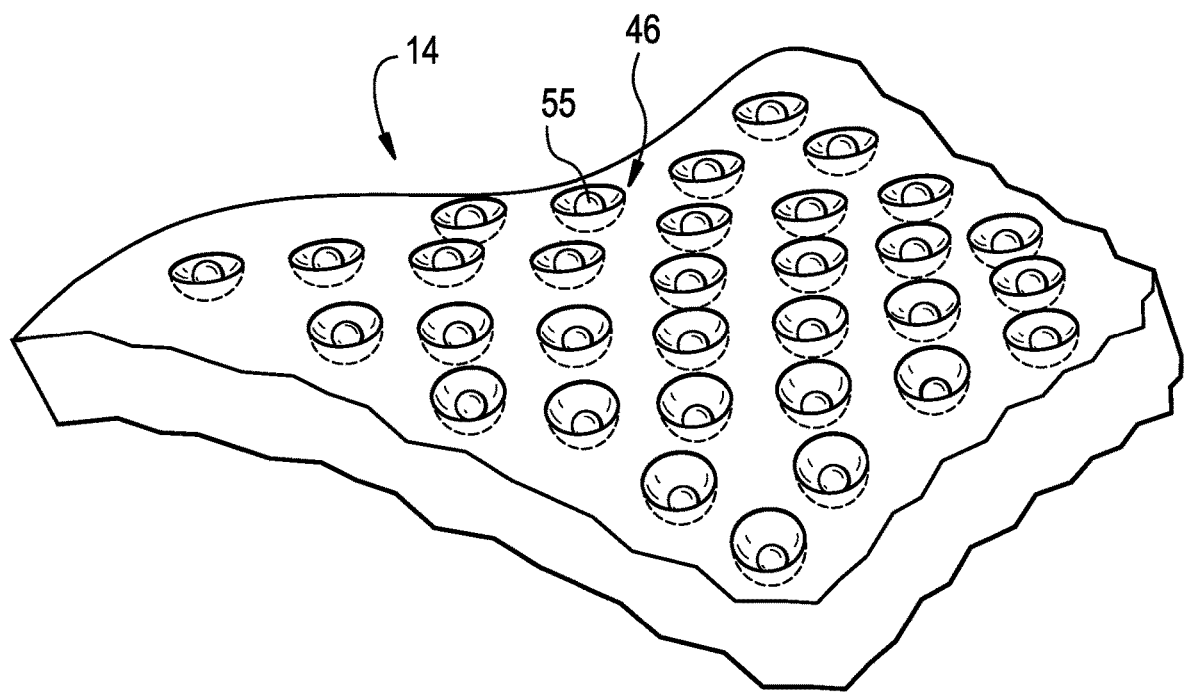
FIG. 4 is a diagrammatic perspective view of a cell culturing substrate including microcavities of the microcavity dish of FIG. 1, according to one or more embodiments shown and described herein.

Referring briefly to FIG. 4, the microcavities 46 of the cell culturing substrate 14 may be rounded including rounded bottom surfaces 48 that can facilitate formation of spheroids 55 within the microcavities 46. The cell culturing substrate 14 may also be formed of a transparent material to allow for viewing or imaging through the cell culturing substrate 14. While the bottom surfaces 48 are illustrated as round, the bottom surfaces may be flat. Further, coatings may be included in the microcavities 46, for example, to promote adhesion and/or release of the spheroids within the microcavities 46.

FIG. 2 also illustrates that the microcavity dish 10 may include a removable lid 50. The lid 50 may include a cover 53 and a sidewall 57 that extends outwardly from the cover 52. In some embodiments, the sidewall 57 of the lid may include an engagement structure 56 (e.g., a thread) that engages a cooperating engagement structure 58 (e.g., a thread) of the sidewall 16 of the dish body 20 to releasably seal the lid against the sidewall 16. As one example, a quarter turn (e.g., 25 degrees) may be used to fully engage the lid 50 against the sidewall 16. In some embodiments, the lid 50 may include a seal member 60 (e.g., formed of an elastomer) that can be used as a sealing surface against the top edge 18. While threads may be used to connect the lid 50 to the sidewall 16, other suitable connections may be used, such as snap-fit, friction-fit, etc.

Figure 5:
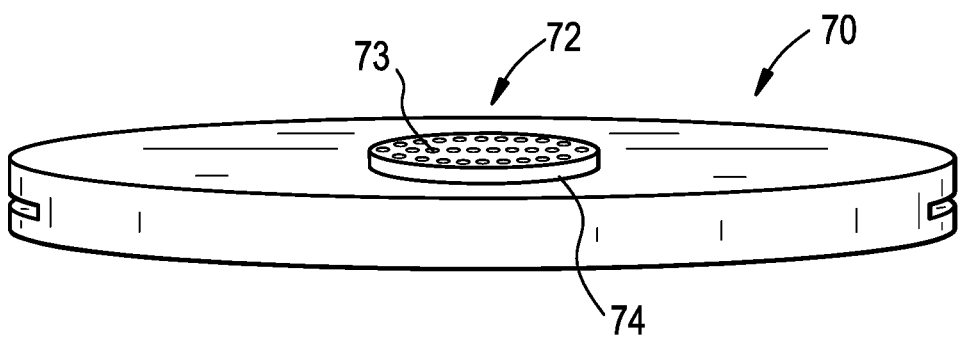
FIG. 5 is a diagrammatic side view of a removable lid for use with the microcavity dish of FIG. 1, according to one or more embodiments shown and described herein.
Figure 6:
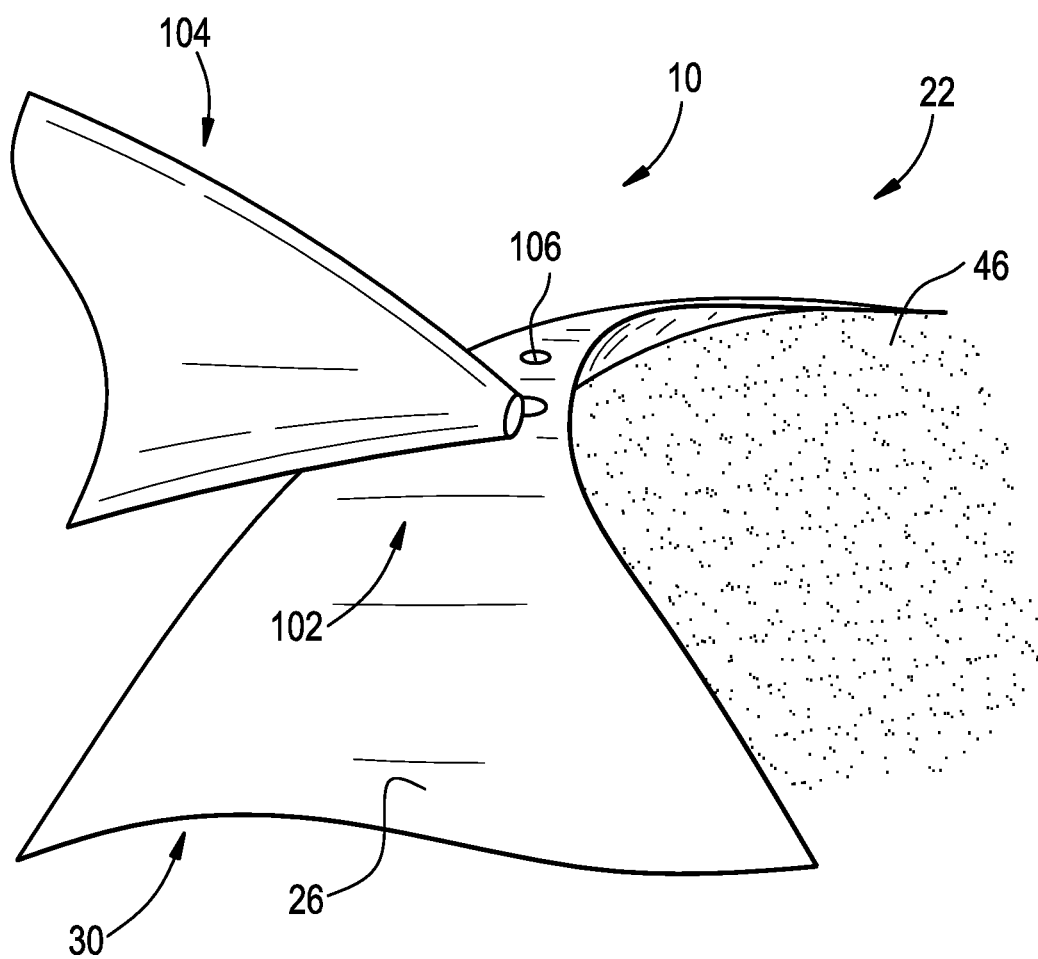
FIG. 6 illustrates operation of the microcavity dish of FIG. 1, according to one or more embodiments shown and described herein.

FIG. 5 illustrates another embodiment of a removable lid 70 that includes many of the features of lid 50. In this embodiment, the lid 70 further includes a vent structure 72 that is provided openings 73 that allow ingress and egress of air or other gas into and out of the cell culture chamber 22. Referring to FIG. 6, a filter 74 may be provided as part of the vent structure 72. The filter 74 can inhibit foreign substances from entering the cell culture chamber 22 through the vent structure 72. However, the vent structure 72 and filter 74 can allow depressurization of the microcavity dish 10 as it progresses through temperature swings from room temperature (approximately 23° C.) to higher incubation temperature (e.g., 37° C.).

Referring to FIG. 6, operation of the microcavity dish 10 is illustrated. A user may remove the lid 50 from the dish body 20 to expose the cell culture chamber 22 and the microcavities 46 of the cell culturing substrate 14. In some embodiments, a cell culture medium may already be located in the cell culture chamber 22. In order to reduce turbulence in the cell culture medium, an end 102 of a liquid transport device 104 (e.g., a pipette) may be inserted into the cell culture chamber 22 and placed on or near the liquid medium delivery surface 26 of the transition portion 30.

With the end 102 of the liquid transport device 104 at a desired location along the liquid medium delivery surface 26, liquid medium 106 may be dispensed onto the liquid medium delivery surface 26 adjacent the cell culture medium already present in the cell culture chamber 22. The transition portion 30 not only provides the liquid medium delivery surface 26 for delivering the liquid medium 106, but also provides a support structure that can support the end 102 of the liquid transport device 104 outside the cell culture medium. The cell culture medium can also be aspirated in a similar fashion using the liquid medium delivery surface 26.

Figure 7:
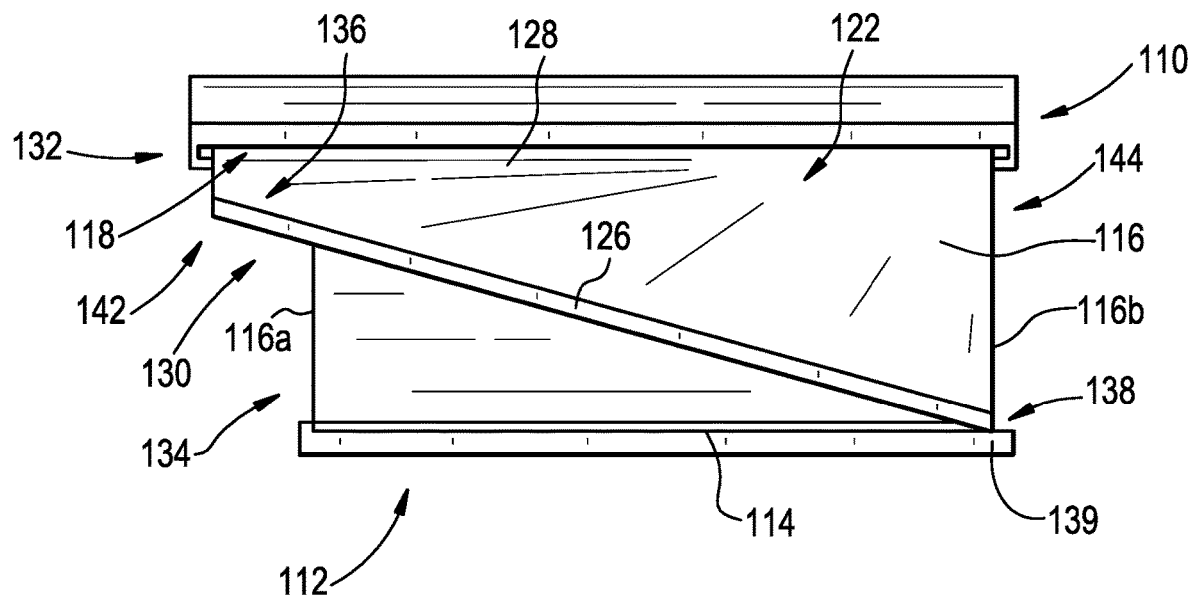
FIG. 7 is a diagrammatic side view of a microcavity dish, according to one or more embodiments shown and described herein.

Referring to FIG. 7, while a circular or other round microcavity dish 10 is described above, other shapes may be used, such as rectangular. In the example of FIG. 7, a rectangular microcavity dish 110 includes many of the features described above including a bottom 112 that includes a cell culturing substrate 114 and a sidewall 116 that extends outwardly from the bottom 12 to a top edge 118. In this embodiment, the sidewall 116 is rectangular and includes sidewall portions enclosing a cell culture chamber 122.

The microcavity dish 110 includes a liquid medium delivery surface 126 that extends along an interior surface 128 of the sidewall 116. The liquid medium delivery surface 126 is defined by a transition portion 130 of the sidewall 116 that divides the sidewall 116 into an upper portion 132 and a lower portion 134 that is offset inward relative to the upper portion 132.

The transition portion 130 and its liquid medium delivery surface 126 has a first end 136 that is near to the top edge 118 and an opposite, second end 138 that is near to a bottom edge 139 of the sidewall 116. The first end 136 may be at one side 142 of sidewall portion 116a and the second end 138 may be at an opposite side 144 of the sidewall portion 116a. In some embodiments, such as the one illustrated, the transition portion 130 extends only along the interior surface 128 of the sidewall portion 116a. However, other sidewall portions may include a transition portion and associated liquid medium delivery surface.

As above, the transition portion 130 extends from the first end 136 toward the second end 138 on a decline. In some embodiments, the slope of the decline of the transition portion 130 may change between the first end 136 and the second end 138. In some embodiments, the slope of the decline of the transition portion 130 may be substantially constant between the first end 136 and the second end 138 or a combination of constant and changing slopes along different segments of the transition portion 130.

Figure 8:
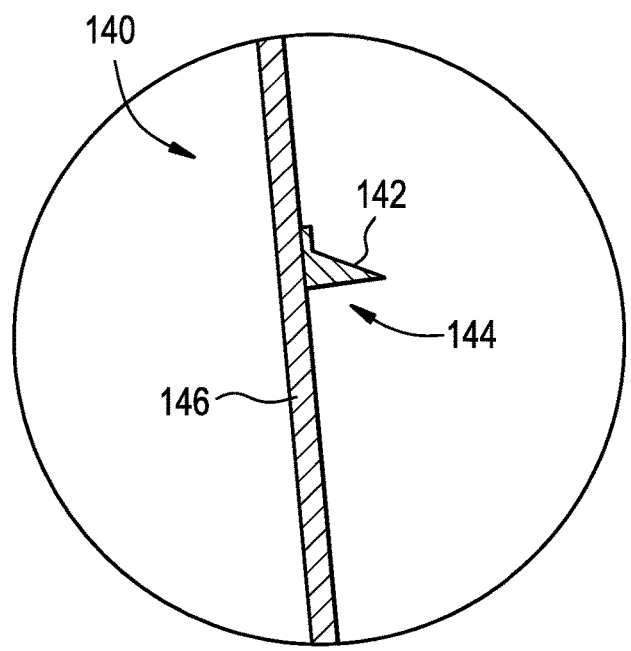
FIG. 8 is a diagrammatic section view of a portion of a microcavity dish, according to one or more embodiments shown and described herein.

Referring to FIG. 8, another embodiment of a microcavity dish 140 may include many of the features described above. In this embodiment, however, a liquid medium deliver surface 142 is formed by a liquid delivery track 144 that is formed separately from sidewall 146 and is attached thereto using any suitable method.

The above-described microcavity dishes include a bottom that can by formed by a cell culturing substrate and a sidewall that extends outwardly from the bottom to a top edge. A liquid delivery track may be formed using a transition portion of the sidewall that divides the sidewall into an upper portion and a lower portion where the lower portion is narrower than the upper portion. The transition portion provides a liquid medium delivery surface that can be used during a fill or aspiration process to reduce turbulence within the cell culture medium within the cell culture chamber of the microcavity dishes. The liquid medium can be delivered along the liquid medium delivery surface to or away from a liquid transport device, such as a pipette with an end of the pipette located on or near to the liquid delivery surface but away from a majority of the cell culture medium already located in the cell culture chamber.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modification and variations come within the scope of the appended claims and their equivalents.

What is claimed is:

1. A microcavity dish for cultivating cells, the microcavity dish comprising:
   a dish body comprising a sidewall that encloses a cell culture chamber within the dish body, the dish body having a top and a bottom, wherein the bottom comprises a cell culturing substrate comprising an array of microcavities, wherein the sidewall extends from the bottom to the top of the dish body and wherein the cell culturing substrate is formed separately from the dish body and is connected thereto;
   the sidewall comprising a liquid medium delivery surface that includes a transition portion that divides the sidewall into an upper portion and a lower portion that is offset inward relative to the upper portion, wherein the liquid medium delivery surface has a first end nearer to the top than the bottom of the dish body and an opposite second end nearer to the bottom than the top of the dish body, wherein the liquid medium delivery surface extends at least partially along an interior surface of the sidewall and slopes along a length of the liquid medium delivery surface downwardly from the first end to the second end and toward the bottom;
   wherein the liquid medium delivery surface is on a portion of the sidewall above the array of microcavities.

2. The microcavity dish of claim 1, wherein the transition portion extends between opposite sides of the sidewall.

3. The microcavity dish of claim 1, further comprising a removable lid that connects to the top of the dish body.

4. The microcavity dish of claim 3, wherein the lid further comprises a vent to release air pressure within the cell culture chamber.

5. The microcavity dish of claim 3, wherein the lid comprises an internal threaded surface that engages an external thread of the dish body to close the lid against the dish body.

6. The microcavity dish of claim 1, wherein the dish body including the upper portion, lower portion and transition portion is formed as a single, monolithic structure.

7. The microcavity dish of claim 1, wherein the dish body is round or rectangular in cross-sectional shape.

8. A microcavity dish for cultivating cells, the microcavity dish comprising:
   a dish body comprising a sidewall that encloses a cell culture chamber within the dish body, the dish body having a top and a bottom, wherein the bottom comprises a cell culturing substrate comprising an array of microcavities, wherein the sidewall extends from the bottom to the top of the dish body and wherein the cell culturing substrate is formed separately from the dish body and is connected thereto; and
   a liquid delivery track that extends along the sidewall and at least partially along the cell culture chamber defining a liquid medium delivery surface, wherein the liquid delivery track has a first end nearer to the top than the bottom of the dish body and an opposite second end nearer to the bottom than the top of the dish body, and wherein the liquid delivery track extends at least partially along an interior surface of the sidewall and slopes along a length of the liquid delivery track downwardly from the first end to the second end and toward the bottom;
   wherein the liquid medium delivery surface is on a portion of the sidewall above the array of microcavities.

9. The microcavity dish of claim 8, wherein, the liquid delivery track extends between opposite sides of the sidewall.

10. The microcavity dish of claim 8, further comprising a removable lid that connects to the top of the dish body.

11. The microcavity dish of claim 10, wherein the lid further comprises a vent to release air pressure within the cell culture chamber.

12. The microcavity dish of claim 10, wherein the lid comprises an internal threaded surface that engages an external thread of the dish body to close the lid against the dish body.

* * * * *